US007182084B2

(12) United States Patent
Cleveland

(10) Patent No.: US 7,182,084 B2
(45) Date of Patent: Feb. 27, 2007

(54) SPICA CHAIR

(76) Inventor: Michael D. Cleveland, P.O. Box 817, Ruidoso, NM (US) 88355

( * ) Notice: Subject to any disclaimer, the term of this patent is extended or adjusted under 35 U.S.C. 154(b) by 548 days.

(21) Appl. No.: 10/225,979

(22) Filed: Aug. 22, 2002

(65) Prior Publication Data

US 2004/0039320 A1 Feb. 26, 2004

(51) Int. Cl.
*A61F 5/00* (2006.01)
*A61G 15/00* (2006.01)

(52) U.S. Cl. ...................... 128/845; 602/32; 280/250.1

(58) Field of Classification Search ............ 602/32–40, 602/24; 128/845, 94; 482/79, 99, 136, 143–146, 482/66–68, 51; 135/65–67, 74–77; 280/304.1, 280/242.1, 648, 647, 650, 250.1, 87.021, 280/87.05, 87.051, 87.041, 655.1, 651, 655; 297/174, 195, 345, DIG. 4, DIG. 10; 248/157, 248/399, 400; 378/208, 209; 5/601, 624; 601/21–32, 34–35, 104, 105
See application file for complete search history.

(56) References Cited

U.S. PATENT DOCUMENTS 2,658,507 A 11/1953 Neufeld
3,029,106 A 4/1962 McGuire
3,509,876 A 5/1970 Pilz
3,599,962 A 8/1971 Henry
4,184,618 A * 1/1980 Jones ......................... 224/407
4,342,451 A 8/1982 Teague
4,552,348 A 11/1985 Forssmann et al.
4,927,167 A * 5/1990 Davis ...................... 280/250.1
5,489,258 A * 2/1996 Wohnsen et al. .............. 602/5
5,556,120 A * 9/1996 Davis ...................... 280/304.1
5,618,055 A * 4/1997 Mulholland ................. 280/641
6,666,796 B1 * 12/2003 MacCready, Jr. ............ 482/51
2003/0098190 A1 * 5/2003 Kanno et al. ............. 180/65.6

* cited by examiner

*Primary Examiner*—Teena Mitchell
*Assistant Examiner*—Shumaya Ali
(74) *Attorney, Agent, or Firm*—Rod D. Baker

(57) ABSTRACT

A lightweight, collapsible and transportable spica chair to be used by toddler, juvenile, and adult patients fitted with a spica cast. Foldable rigid frame supports mutually inclining and individually adjustable rest surfaces including a torso pad assembly and an adjustable leg support assemblies. The patient is supported at the stomach/torso region and at the legs so that the patient is able to "sit" comfortably in a semi-upright position for extended periods of time. An optional tray assembly permits the patient to place items of interest, such as food or toys, within easy reach.

30 Claims, 8 Drawing Sheets

SPICA CHAIR

BACKGROUND OF THE INVENTION

1. Field of the Invention (Technical Field)

The present invention relates to medical devices and more particularly to a lightweight, collapsible and portable spica chair for patients who have been fitted with a spica-type cast.

2. Background Art

Certain types of human medical conditions, particularly hip surgeries, fractured femurs, and pelvic fractures, may require the placement of a spica cast upon the recuperating patient. A “spica cast” is a rigid cast covering most of the patient’s pelvic region, and usually both thighs. Also, the cast often extends below the patient’s knee, usually to the foot, of the leg with the affected hip or femur. The upper legs (femurs) are maintained in a “straight” position, i.e., the position they would be in were the patient standing upright. The spica cast immobilizes the patient’s hips, and thus generally prevents the patient from assuming a normal sitting position. A spica cast often, but not universally, has a rigid stabilizing bar extending between its thigh portions. FIG. 1 illustrates a patient wearing a typical spica cast. A spica cast may be composed of any of the conventional materials for the making of orthopedic casts, such as plaster of Paris, but including lightweight fiberglass and other known cast materials. For a variety of reasons, spica cast patients frequently are children.

Wearing a spica cast poses a number of serious discomforts and impediments to the patient. A serious problem—one solved by the present invention—is the inability of the patient to assume a normal sitting position. This restriction makes it difficult to participate in many ordinary daily activities, even those that most persons fitted with other types of casts can enjoy, such as writing, watching television, eating, and other activities commonly performed in a sitting position. The fact that spica casts often are worn for many weeks, sometimes months, gives rise to the need for an apparatus for permitting spica cast patients to enjoy a comfortable upright position. This is particularly true for the child patient, whose rehabilitation is significantly promoted if he can “sit” upright rather than remain prone upon a floor or bed. Further, even adult patients are more likely to develop pneumonia and other respiratory and/or sinus distress when unable to spend appreciable time in an upright position.

It is desirable, therefore, to provide a chair that is useable by a spica cast patient.

U.S. Pat. No. 2,658,507 discloses an immobile fracture table meant for examination of a patient, the setting of fractures, application of bandages, casts and the like. This device is intended for use in a physician’s office, and no mention is made of a spica cast.

U.S. Pat. No. 3,029,106 discloses a non-portable surgeon’s operating chair, particularly to a combined seat and chest support device for supporting a person in a comfortable position while performing a surgical procedure. The chair is designed to support the physician, not the patient, during a surgical procedure.

U.S. Pat. No. 3,509,876 discloses a medical device equipped with arm rests which can be moved into and out of a variety of positions. No spica cast uses are indicated.

U.S. Pat. No. 3,599,962 discloses a medical device used in a physician’s office to aid in supporting the trunk and lower extremities of a patient to allow free access for placement of casts.

U.S. Pat. No. 4,552,348 teaches a couch for reclining a completely or partially anesthetized patient. The device purports to prevent an anesthetized patient from having compression sites that would block blood circulation. No disclosure is made of use by patients in a spica cast; indeed, the device is expressly indicated for submersible use under water by patients undergoing kidney stone treatments.

A need remains, therefore, for a chair that is adapted for everyday use by a patient fitted with a spica cast.

SUMMARY OF THE INVENTION (DISCLOSURE OF THE INVENTION)

A primary object of the present invention is to provide patients in a spica cast, especially children, a fully adjustable chair which allows them to sit in a position that is comfortable and allows for hands-free movement. A primary advantage of the present invention is that it supports a spica cast patient in relative comfort for extended periods of time. A padded torso support can be movably adjusted to a wide variety of locations and angles and temporarily fixed into a desired position. Two leg supports also can be adjusted to, and temporarily fixed in, different positions. Accordingly, the inventive chair can be adapted to receive and support patients of different sizes, as well as different patients whose spica cast holds their body in a particular position. The spica chair optionally features an adjustable tray where the patient may place items in immediate reach. The inventive chair has collapsible joints that allows it to be folded or collapsed for storage or transport, and preferably is made of lightweight materials to promote portability.

The invention disclosed here is distinctive over prior art devices as it is designed to be used for patients already in a spica cast rendering them immobilized from the hip to the knees. Because of the awkwardness of the cast it is very difficult for the patient to sit comfortably for extended periods of time. The present invention allows the patient in a spica cast to have his body supported at three points and in such a way that adjustments can be made at several different levels to accommodate the patients needs. The invention is also intended to be used by all sizes of patients, including infants, toddlers, and adults and its light weight and collapsibility allows it to be used in the home as well as in a hospital.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DESCRIPTION OF THE PREFERRED EMBODIMENTS (BEST MODES FOR CARRYING OUT THE INVENTION)

The present invention relates to medical devices, particularly medical furniture, and specifically a specialized chair for use by a person wearing a spica cast. Spica casts are rigid orthopedic casts used to immobilize a patient's pelvic region. Often, a patient who has undergone certain surgery or other treatment to the hips or hip joint(s) wears a spica cast. The present invention is a chair adapted for use by a person wearing a spica cast (or otherwise afflicted with immobile hip joints) to permit the person to "sit" in an upright position to eat, write, enjoy television, play a board game, or the like. It is intended to be used by the patient at home, or at a hospital. The adaptability, adjustability, and portability of the apparatus of the invention may promote its repeated re-use by a series of different patients; thus, the invention will find beneficial use in hospitals and rehabilitation facilities that care for many different spica cast patients over time. The invention could also be rented to a given patient for a limited period of use at home.

Figure 1:
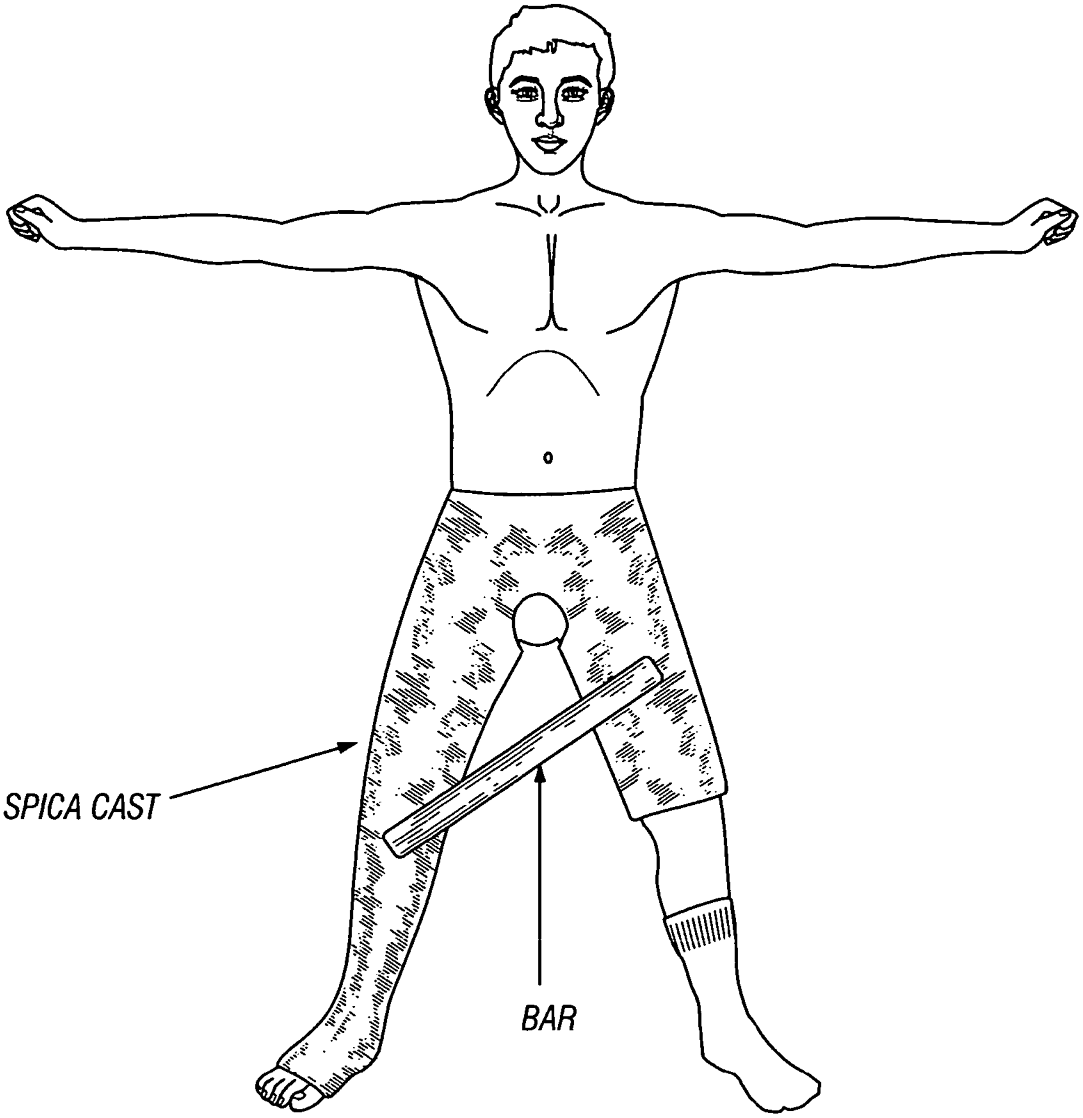
FIG. 1 (Prior Art)
FIG. 1 is from the prior art, and simply depicts a patient wearing a typical spica cast.

In use, the invention permits the patient to enjoy a mostly upright position, despite the fact that the patient cannot assume a normal "sitting" position. In the usual sitting position, a person's thighs (as supported upon the femur bones) are about perpendicular to the spine. A spica cast, however, fixes the patient's thighs approximately parallel to the spine, i.e., in a "standing" position (FIG. 1). Nevertheless, the present invention allows a person wearing a spica cast to be situated in an upright, forward-facing position, with his or her weight borne by the torso and legs.

Figure 2:
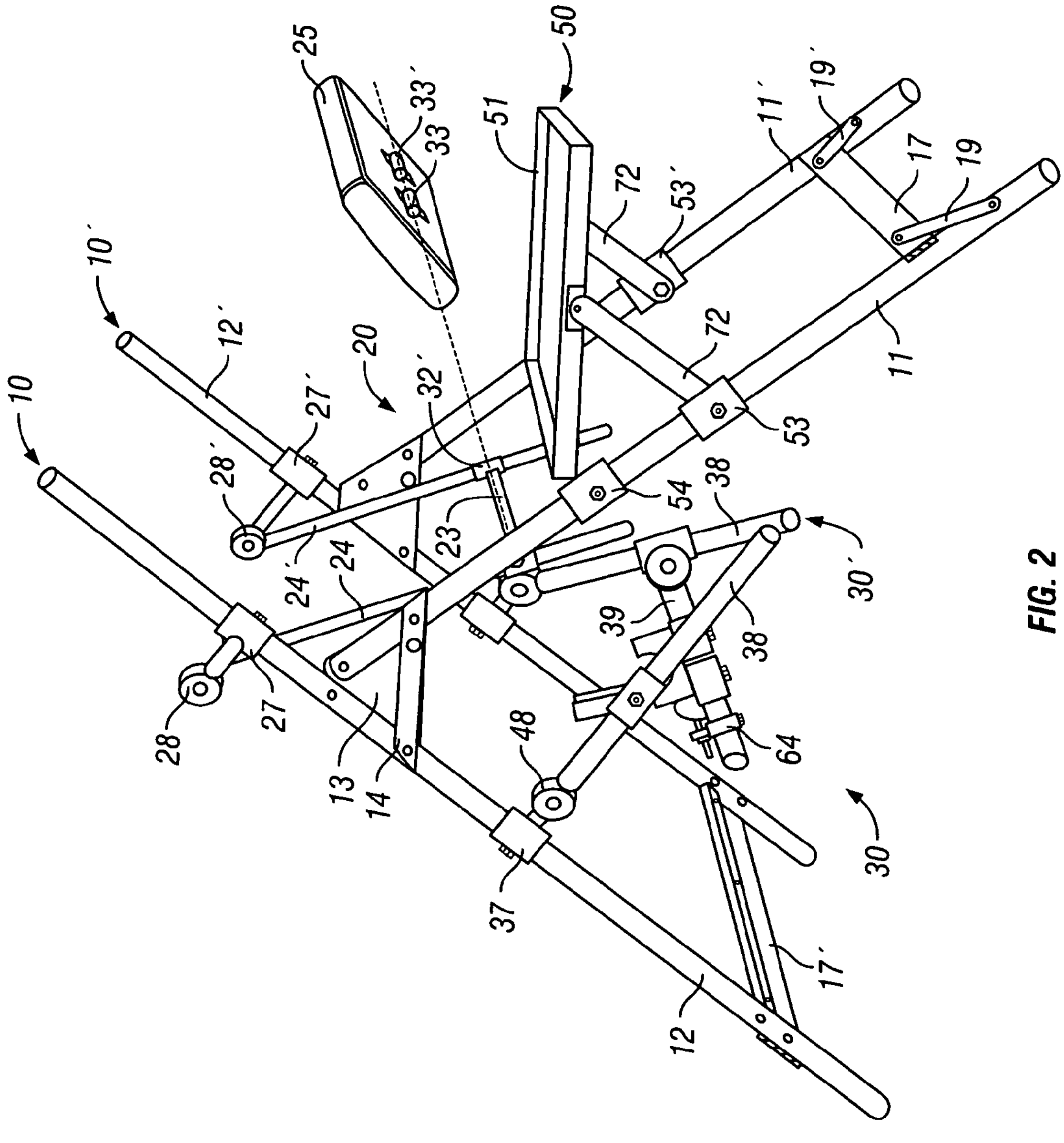
FIG. 2 is a perspective, partially exploded side view of a preferred embodiment of the apparatus of the present invention, depicting the principal assemblies of the spica chair, the torso pad shown detached for clarity of illustration.
Figure 3:
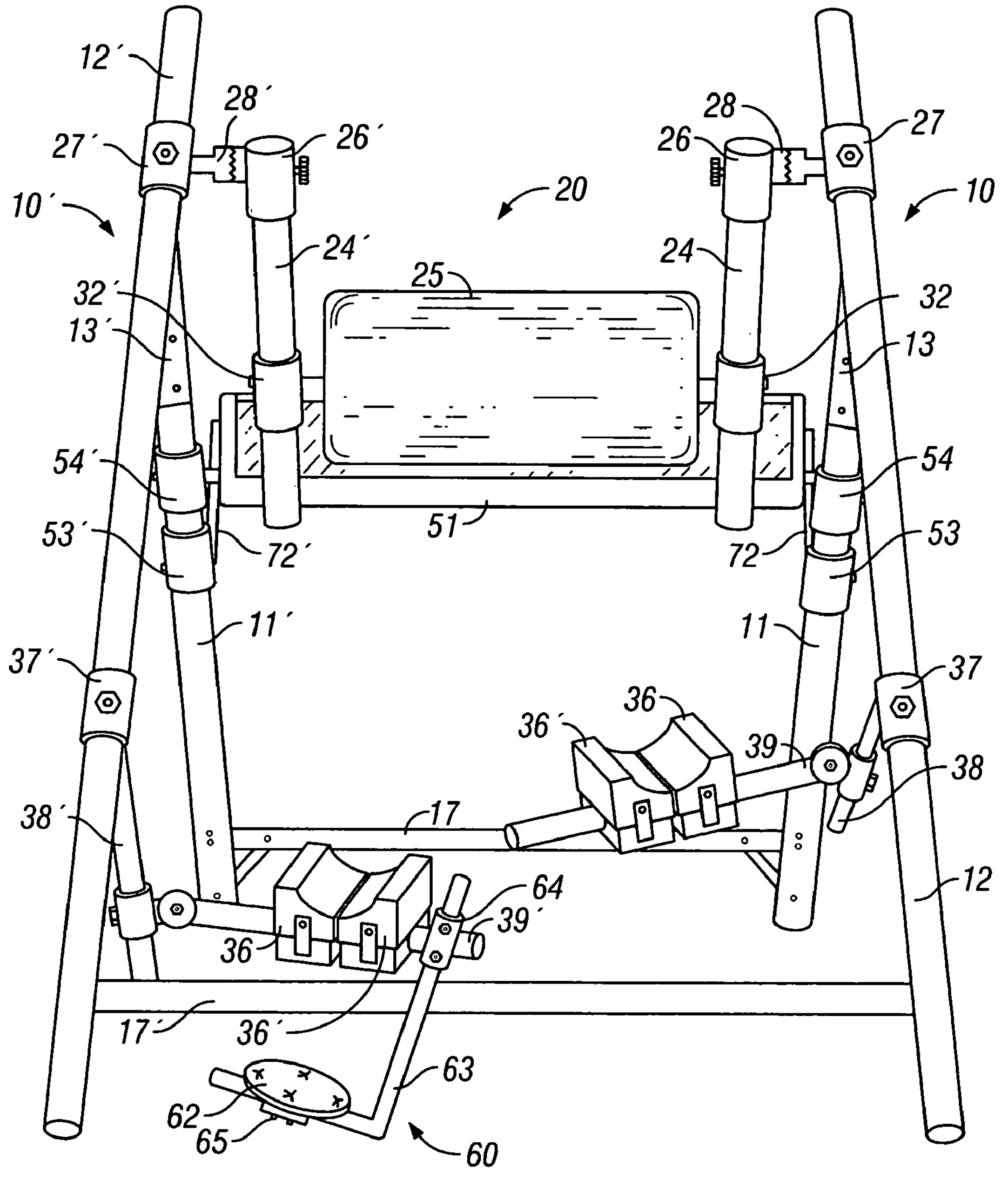
FIG. 3 is a rear perspective view of a preferred embodiment of the invention.

Attention is invited to FIGS. 2–3, depicting the complete spica chair apparatus according to the present invention. The apparatus is a composite of six principal sub-assemblies. Two essentially identical, parallel, frame assemblies 10, 10' provide the basic foundation for the apparatus. Disposed between the frame assemblies 10, 10' are a torso support assembly 20 upon which the patient's thorax or abdomen is supported, a pair of leg assemblies 30, 30' for supporting the patient's legs, and an optional tray assembly 50 for receiving and supporting food and eating utensils, a game, writing paper and pencil, or the like. The principal structural components of the apparatus preferably are fashioned from lightweight metal tubes, such as tubular steel or aluminum of, for example, 2.5 to 6.0 cm outside diameter.

The frame assemblies 10, 10', torso support assembly 20, tray assembly 50 and leg assemblies 30, 30' are assembled as further explained herein to provide a lightweight, portable, adjustable, collapsible spica chair for use by a person fitted with a spica cast. The apparatus of the invention can be manufactured-in a variety of sizes to meet the needs of patients of different sizes, ranging anywhere from toddlers to adults. However, an advantage of the invention is that its various assemblies are adjustable to accommodate patients of somewhat different sizes, so it likely is possible to meet the needs of nearly all patients by manufacturing the invention in just three or four different sizes.

Reference numerals 10 and 10' designate two frame assemblies for supporting the apparatus upon the ground or floor. The frame assemblies 10, 10' are substantially identical, except that one is the reverse image of the other, so that description of the right frame assembly 10 serves as well to describe the left frame assembly 10'. The two frame assemblies 10, 10' are generally parallel when the invention is in use, although they may be inclined somewhat towards each other (i.e., with their tops closer together than their bottoms) for enhanced lateral stability of the apparatus.

Figure 4B:
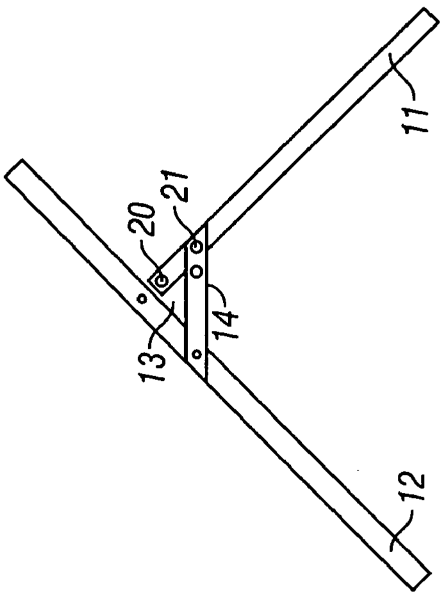
FIG. 4B is a side view of the assembled right frame assembly elements of the apparatus according to the present invention, shown in the extended position for use.
Figure 4C:
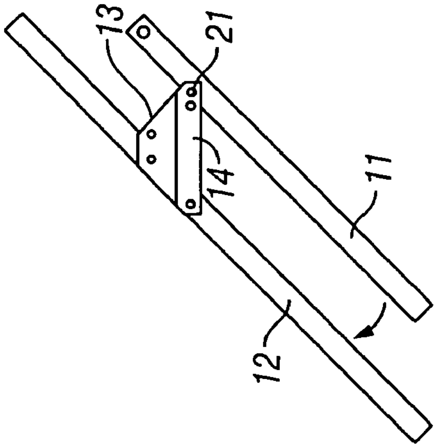
FIG. 4C is a side view of the assembled right frame assembly, showing how it may be moved into a collapsed position.
Figure 4A:
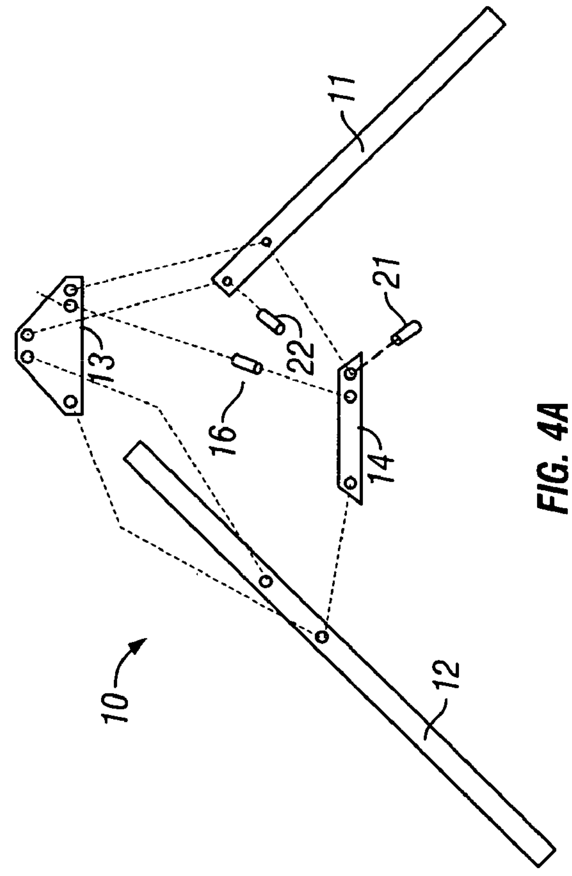
FIG. 4A is an exploded view of the right frame support assembly, the left frame support assembly being substantially identical except being a mirror-image of the right.

As seen in FIGS. 2 and 3, and disclosed in detail by FIG. 4B, frame assembly 10 essentially is a modified A-frame. The A-frame design provides excellent stability at a minimum of weight and materials expense. Front and rear main frame members 11, 12 are joined, as by pin-and hole connections, with a frame plate 13 and a stabilizer bar 14 to define a strong and stable triangular frame to support the other assemblies of the chair. The assembled left and right main frame assemblies 10, 10' are connected laterally and mutually supported in the front and rear by lateral frame bars 17, 17'. Cross braces 19, 19' optionally but preferably interconnect the front main frame members 11, 11' and lateral frame bar 17 to enhance frame vertical stability. Referring to FIGS. 4A–4C, it is seen that a hinge pin 21 supplies a pivotal connection between the front main frame member 11 and stabilizer bar 14 to permit the apparatus to be extended or collapsed. A lock pin 22, retractably insertable through the proximate end of the front main frame member 11 and into a corresponding hole in the frame plate 13, is used to lock the frame assembly 10 in the extended position seen in FIG. 4B. Referring to FIG. 4C, it is seen that the lock pin 22 may be retracted or removed, and the front main frame member 11 rotated about the hinge pin 21, to permit the front main frame member 11 to be pivoted toward the rear main frame member 12. The two main frame members 11, 12 therefore may be moved into a nearly parallel relation when the overall chair apparatus is collapsed for storage or transportation, as suggested by the directional arrow in FIG. 4C.

When the frame assembly 10 is in the extended position for use (FIG. 4B), the proximate end of the front main frame member 11 may abut the wall of the rear main frame member 12 to transmit loads directly between the main frame members 11, 12 to reduce loading and shear in the frame plate 13. FIGS. 4A and 4B show a leg stop tube 16 installed between the frame plate 13 and the stabilizer bar 14 in a position relational to the front frame member 11 to provide a stop for the front frame member in the fully extended use position. It will be immediately recognized by one skilled in the art that the bottom end of each frame member 12, 12', 11, 11' can be fitted with wheels or casters, if desired, to enhance mobility.

Figure 5:
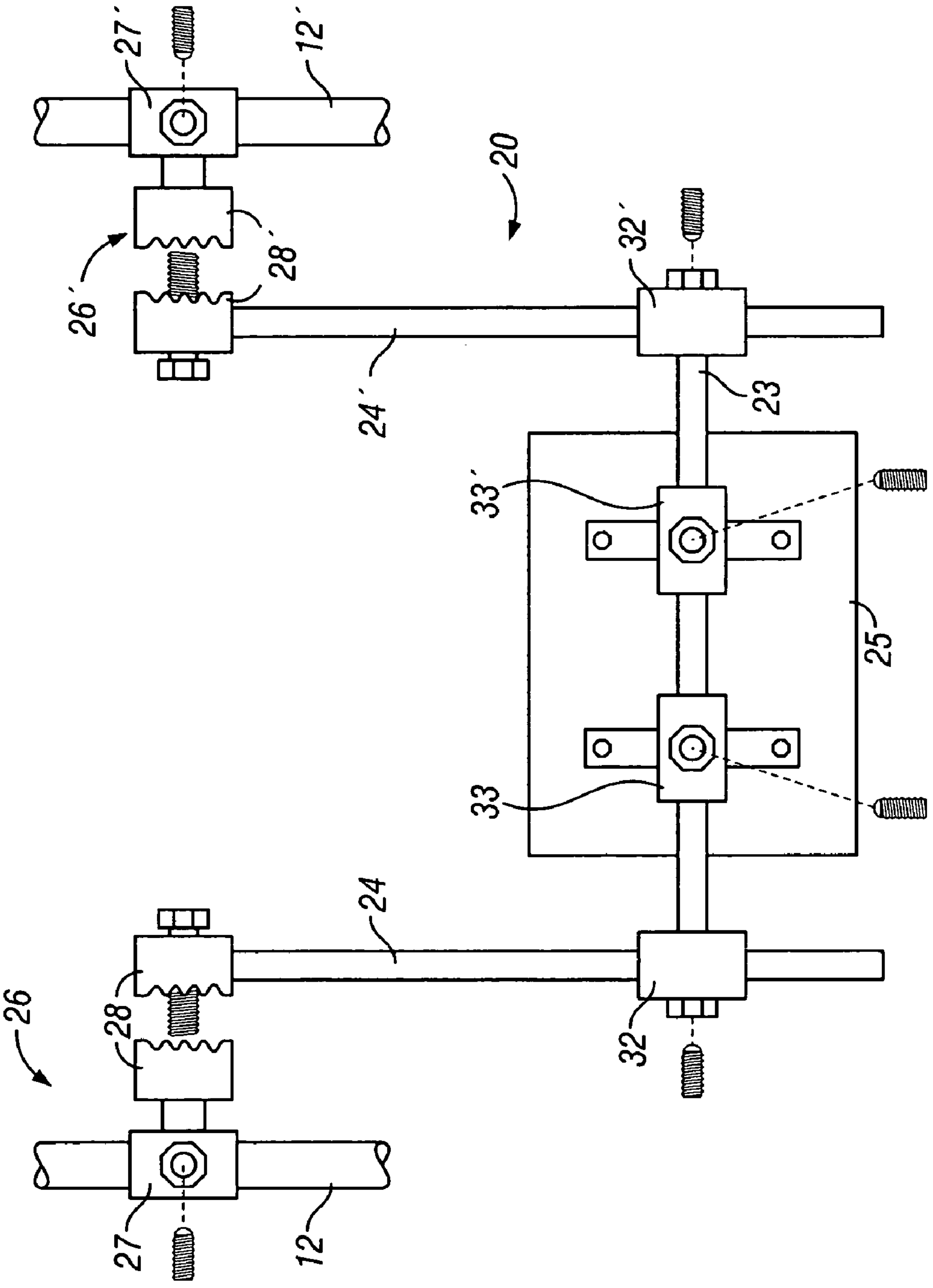
FIG. 5 is an enlarged bottom view, partially exploded, of the torso support assembly portion of an embodiment of the apparatus of the invention.

The torso support assembly 20 supports and bears the weight of the patient's upper torso, while the patient's legs are supported in the leg support assemblies 30, 30'. FIGS. 3 and 5 show that the torso support assembly 20 features a usually horizontal torso pad bar 23, a pair of torso pad adjusting bars 24, 24', and an adjustable-pitch torso pad 25. Torso support assembly 20 is attached to the upper segments of each of the rear main frame members 12, 12' as indicated in FIGS. 2 and 3. An advantage of the invention is that the position of the torso support assembly 20 is fully adjustable, since the torso support assembly is selectively positionable upon the frame assemblies 10, 10', and the torso pad bar 23 is selectively positionable along the torso pad adjusting bars 24, 24'. Referring especially to FIG. 5, each of torso collar assemblies 26, 26' consists of an adjustable locking collar 27, 27' and a lockable pivot connector 28, 28'. Adjustable locking collars 27, 27' are of known construction, and are slidable along the upper segment of the rear frame members 12, 12'. Each collar 27, 27' has a set screw or other suitable releasable locking element, so that when the locking element is released, the collar assembly 26 or 26' can be selectively moved to a desired position upon the rear frame member 12 or 12'. The locking element can then be tightened or engaged to fix temporarily the collar 26 or 26' in the desired position upon the frame assemblies 10, 10'. Attached to the adjustable locking collars 27, 27' are pivotally adjustable pivot connectors 28, 28' which allow the torso pad adjusting bars 24, 24' to be controllably pivoted (in one plane) with respect to the rear main frame members 12, 12'. Pivot connectors 28, 28' are of a known construction, having confronting inter-engageable frictional, notched, or toothed portions. The pivot connectors 28, 28' can be fixed against pivotal movement by tightening (as by a joining bolt) the toothed portions into locked engagement. Connectors 28, 28' can likewise be released to disengage the toothed portions to permit the connectors to pivot freely, so that the angular relation between each torso pad adjusting bar 24, 24' and its corresponding frame member 12, 12' is fully adjustable. When the desired angular relationship is obtained, the pivotal connectors 28, 28' are temporarily locked to secure the desired angle. It is seen, therefore, that the height of the torso pad adjusting bars 24, 24' above the floor is selectively adjustable and temporarily fixable by means of the locking collars 27, 27', while the angles of the torso pad adjusting bars 24, 24' with respect to the floor is adjustable and temporarily fixable by means of the lockable pivot connectors 28, 28'.

Continued reference is made to FIGS. 3 and 5. The torso pad bar 23 is connected to the torso pad adjusting bars 24, 24' by means of pad bar collars 32, 32'. Pad bar collars 32, 32' are similar in construction to locking collars 27, 27', and are slidable along the torso pad adjusting bars 24, 24'. The position of the torso pad bar 23 in relation to the torso pad adjusting bars 24, 24' thus can be selected by the simple expedient of loosening the collars 32, 32', sliding them into the desired positions along the torso pad adjusting bars, and then tightening a set screw or engaging some other suitable locking element temporarily to fix the collars 32, 32' in place.

Accordingly, the torso support pad 25 can be selectively located in three-dimensional space, and be vertically and horizontally moved to a desired position and there firmly locked into place, by selective loosening, sliding and tightening of the locking collars 27, 27' and 32, 32', and by the releasable-lockable pivoting of the lockable pivot connectors 28, 28'.

The torso support pad 25 is a cushioned, upholstered pack or pad mounted upon a rigid backing board or pan. Pad 25 is devised to provide a comfortable rest or support for the patient's torso, i.e., chest and/or upper abdomen. Optionally but not necessarily, the torso pad 25 may be provided with a belt or strap (not shown) that is securable around the patient, especially a young child, to hold the patient in place upon the pad. Such a belt or strap may be padded and connectable with hook-and-loop fabric fasteners, a buckle, or the like, so that the patient is prevented from sliding off the pad 25.

As illustrated by FIG. 5, the pad 25 is movably mounted upon the torso pad bar 23. The torso pad bar 23 is attached to the torso pad bar collars 32, 32'. The torso pad 25 itself is pivotally mounted upon the torso pad bar 23 by means of one or more torso pad collars 33, 33'. Like the other collars described herein above, pad collars 33, 33' can be selectively loosened or released by means of a set screw or other suitable releasable locking element, so that the pad 25 can be moved back and forth along the length of the torso pad bar 23, as well as rotate or pivot in relation to the pad bar 23. As an advantageous result, the lateral position of the torso support pad can be selected and temporarily fixed, as well as the "pitch" of the pad 25, i.e., the angle between the pad and horizontal.

Consequently, the absolute position of the torso support pad 25 is optimally and selectively variable. The user can select and temporarily fix the height of the pad 25 above the floor by manipulating and setting the positions of the torso collar assemblies 26, 26' upon the frame assemblies 10, 10', and the positions of the pad bar collars 32, 32' upon the torso pad adjusting bars 24, 24'. The horizontal position of the pad 25 front-to-back within the apparatus can be selected and releasably fixed by manipulating, pivoting, and locking the lockable pivot connectors 28, 28' at the desired angle. As seen in FIG. 2, the torso pad adjusting bars 24, 24' thus can be angled forward and downward within the frame assemblies 10, 10', to situate the torso pad 25 forwardly (to the right in FIG. 2) in the apparatus and in the vicinity of the optional tray assembly 50. Finally, the lateral or side-to-side horizontal position of the torso pad may be selected and releasably fixed using the torso pad collars 33, 33', which also permit the angle or tilt of the pad 25 with respect to horizontal also to be adjusted and set for patient comfort.

Figure 6:
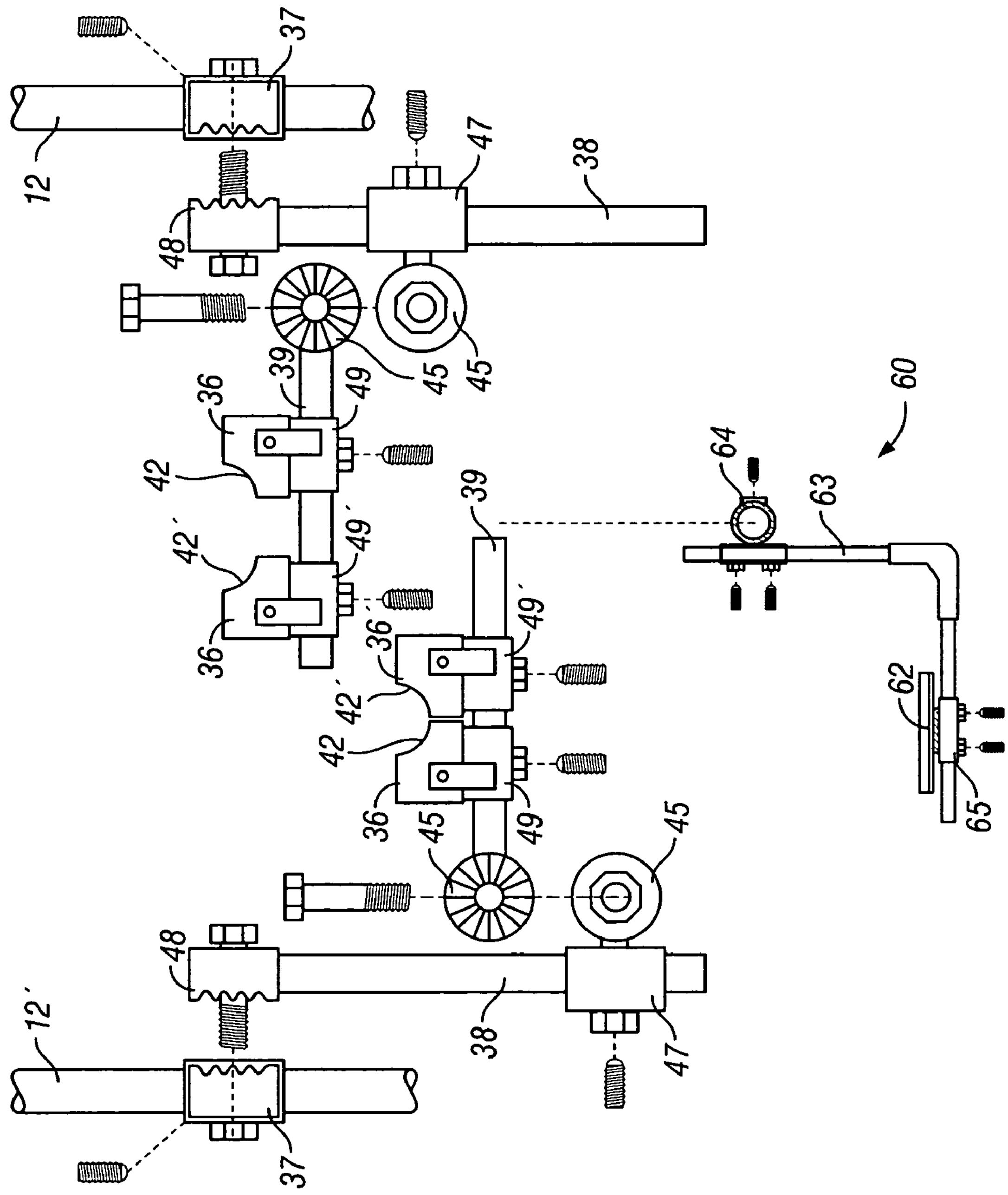
FIG. 6 is an enlarged, partially exploded rear view of the leg support assemblies of an embodiment of the apparatus of the invention.

Description of the leg support assemblies 30, 30' is had with combined reference to FIGS. 3 and 6. The leg support assemblies 30, 30' serve to position and support the legs of a patient in a spica cast. Each leg support assembly 30 or 30' features two substantially identical sets of leg support cradle blocks 36, 36' generally conforming to the shape and size of a patient's leg, although the blocks 36, 36' are adjustable to accommodate legs of different sizes and with or without a cast. Optionally, the blocks 36, 36' may be provided with belts or straps (not shown) to hold the patient's leg in the cradle. The leg support assemblies are substantially identical so that description of the right side assembly 30 serves to describe both, except where noted herein.

Each of the leg support assemblies 30, 30' includes a leg support adjusting bar 38 and a leg cradle adjusting bar 39. The leg support adjusting bar 38 is movably attached to the lower rear main frame member 12 by means of a lockable leg support adjusting locking collar 37, similar in configuration and function to the torso pad locking collars 27, 27' described above. The leg support adjusting collar 37, employing a set screw or other suitable releasable locking element, can slide along the lower portion of the rear main frame member 12 to a desired position and then firmly but releasably locked into place. Accordingly, the location of the connection between the leg support adjusting bar 38 and the rear main frame member 12 is selectively adjustable.

Combined with the leg support adjusting collar 37 is a pivotally adjustable pivot connector 48, which allows the leg support adjusting bar 38 to be controllably pivoted with respect to the rear main frame member 12. Pivot connector 48 is the same or similar to the pivot connector 28 described herein above, having confronting notched, toothed, or frictionally engageable portions. The pivot connector 48 thus can be fixed against pivotal movement by engaging the toothed or frictional portions, or released by disengaging those portions to permit the connectors to pivot freely. Therefore, the angular relation between each leg support adjusting bar 38 and its associated frame member 12 or 12' is fully adjustable. When the desired angular relationship is obtained, the pivotal connectors 48 is temporarily locked to secure the desired angle. The height of the leg support adjusting bars 38 above the floor is selectively adjustable and temporarily fixable by means of the locking collars 37, while the angle of the leg support adjusting bar with respect to the floor is adjustable and temporarily fixable.

Continued reference is made to FIGS. 3 and 6. The leg cradle adjusting bar 39 is connected to the leg support adjusting bar 38 by a cradle bar collar 47. Cradle bar collar 47 is similar in construction to locking collar 27 previously described, and is slidable along the leg support adjusting bar 38. The position of the leg cradle adjusting bar 39 in relation to the leg support adjusting bar 38 thus can be selected by loosening the collar 47, sliding to the desired location along the leg support adjusting bar, and tightening a set screw or engaging some other suitable locking element temporarily to fix the collar 47 in place.

Accordingly, the cradle blocks 36, 36' can be selectively located in three-dimensional space, and be vertically and horizontally moved to a desired position and there firmly locked into place, by controlled loosening, sliding and tightening of the locking collars 37 and 47, and by the releasable-lockable pivoting of the lockable pivot connectors 48.

Reference is made especially to FIG. 6. The leg cradle blocks 36, 36' are solid, and may be made from practically any substantially rigid material, including plastic. The cradle blocks 36, 36' define arcuate supporting surfaces 42, 42' having definitional radii very approximately corresponding to the radius of a typical patient's leg, so that the contour of the cradle surfaces 42, 42' (considered together, defining an approximate semi-circle) is generally complementary to the patient's leg. Cradle blocks 36, 36' optionally are padded or cushioned at the arcuate supporting surfaces 42, 42'.

As illustrated in FIG. 6, the cradle blocks 36, 36' are movably mounted upon the leg cradle adjusting bar 39. Each cradle block 36 or 36' is itself pivotally mounted upon the leg cradle adjusting bar 39 by means of cradle collars 49, 49'. Like the other collars described herein above, pad collars 49, 49' can be selectively loosened or released by means of a set screw or other suitable releasable locking element, so that the cradle block 36 or 36' can be moved back and forth along the length of the leg cradle adjusting bar 39, as well as rotate or pivot in relation to the leg cradle adjusting bar. As an advantageous result, the longitudinal positions of each cradle block 36 or 36' upon the cradle adjusting bar 39 are adjustable independently of each other, and can be selected and temporarily fixed. Also the "pitch" of each cradle block 36 or 36', i.e., the radial position of each block upon the cradle adjusting bar 39, is completely adjustable.

Consequently, the absolute positions of the cradle block 36 or 36' are optimally and selectively variable. The user can select and temporarily fix the height of the blocks 36, 36' above the floor by manipulating and setting the positions of the collars 37 and 47 upon the frame member 12 and the leg support adjusting bar 38 and the positions of the cradle block collars 49, 49' upon the leg cradle adjusting bars 39. The horizontal position of the cradle block 36 or 36' front-to-back within the apparatus can be selected and releasably fixed by manipulating, pivoting, and locking the lockable pivot connectors 45 and 48 at the desired angle. As seen in FIGS. 2 and 3, the leg cradle adjusting bars 39 thus can be angled rearward and downward within the frame assemblies 10, 10', to situate the cradle block 36 or 36' rearwardly (to the left in FIG. 3) in the apparatus to support the patient's legs when the apparatus is in use. Finally, the lateral or side-to-side horizontal positions of the cradle blocks 36, 36' may be selected and releasably fixed using the cradle collars 49, 49', which also permit the angle or tilt of the cradle blocks with respect to horizontal also to be adjusted and set for patient comfort.

Notably, since each of the cradle blocks 36, 36' is independently movable along the leg cradle adjusting bar 39, the relative positions of the cradle blocks can be adapted to accommodate the size of the patient's leg to be received thereon, including, as needed, the surrounding cast. Thus, the cradle blocks 36, 36' can be selectively positioned to comfortably support a patient's thigh or calf, with or without a cast, as the situation may require.

In ordinary use, the apparatus of the invention supports the patient in an inclined position, that is, the torso pad 25 is positioned considerably higher above the floor than the leg support assemblies 30, 30'. The patient is placed with her chest or abdomen upon the torso pad 25 and the front of her thighs, or her shins, or one shin and one thigh, upon a corresponding pair of cradle blocks 36, 36'. Accordingly, some means for preventing the patient from slipping or sliding down off the apparatus, by the force of gravity, is desirable. Reference to FIGS. 3 and 6 shows that either one or both the leg support assemblies 30, 30' preferably is provided with a foot support pad assembly 60. The foot support pad assembly is situated so that the bottom of the patient's foot can rest upon the pad 62, thereby supporting the patient in the spica chair apparatus and preventing the patient's downward slipping or shifting. While only one support pad assembly 60 is shown in the drawing figures, it will be immediately understood that two such assemblies, one mounted upon each leg cradle adjusting bar 39, 39', may be deployed if desired.

Each support pad assembly 60 includes a pad stirrup 63, which may consist of a pair of tubes or rods fixed together to define a fixed angle, such as a right angle, as seen in FIG. 6. The stirrup 63 functions to maintain and support the pad 62 in relation to the leg cradle adjusting bar 39. Upper pad collar 64 and lower pad collar 65 are similar or identical to the collars 27, 33, 37 previously described. Upper pad collar 64 is movable axially along, and is rotatable about, the leg cradle adjusting bar 39 to permit selective adjustment, and temporary fixation, of the position of the stirrup 63. The lower pad collar 65 is movable and lockable in position along the lower strut of the stirrup 63, allowing adjustability of the position of the foot pad 62 upon the stirrup 63. It is apparent that the absolute location of the foot pad 62, in relation to the floor, is highly selectable.

Figure 7:
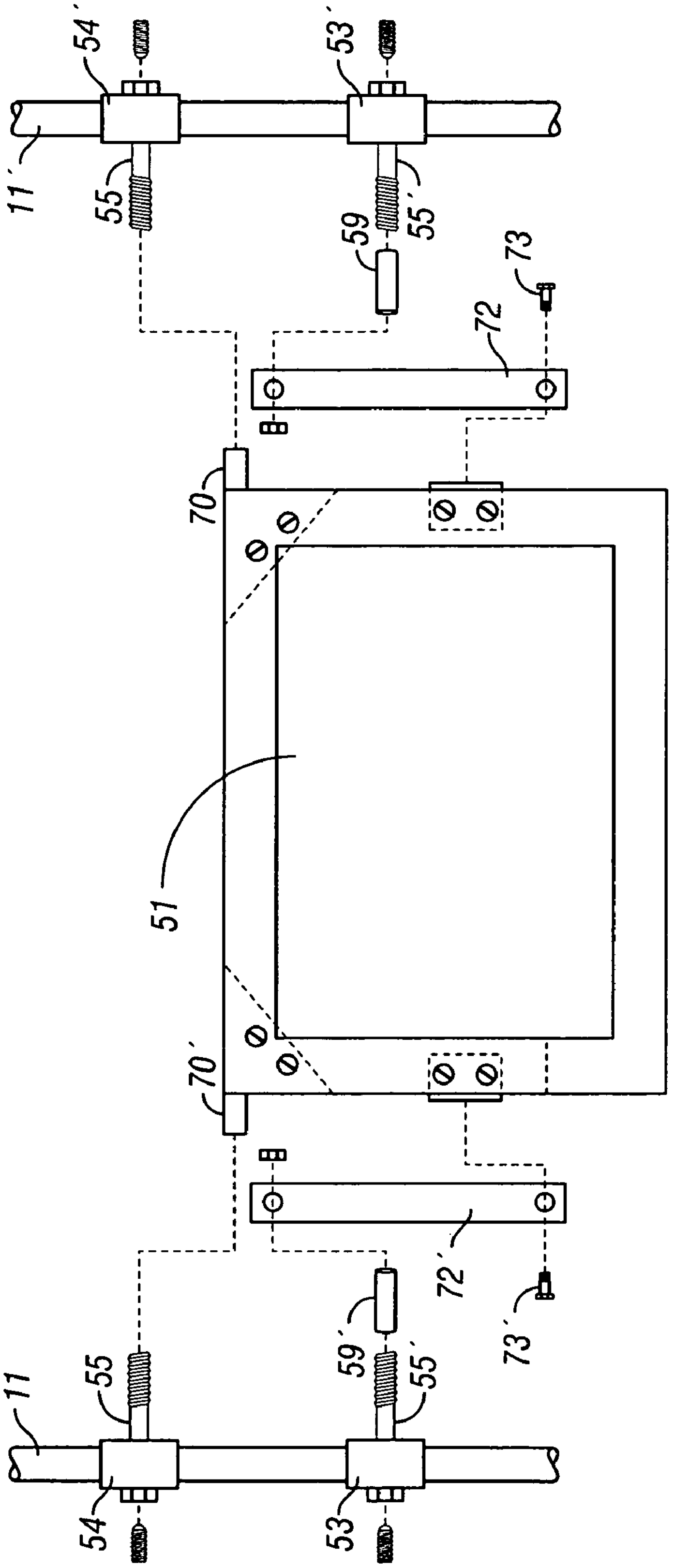
FIG. 7 is an enlarged exploded top view of the tray assembly portion of an embodiment of the apparatus of the invention.

The spica chair apparatus of the invention optionally includes a tray assembly 50, as illustrated in FIGS. 2 and 7. The tray assembly includes a tray 51 made of lightweight metal, wood, plastic or the like, upon which items of interest may be placed for use by the patient. Particular reference is made to FIG. 7. The tray 51 attaches to the front main frame members 11, 11' by two pairs of tray support adjusting collars 53, 53' and 54, 54', which can be moved up and down vertically on the front main frame members, and releasably fixed at a desired position. The upper tray support adjusting collars 54, 54' are connected to the tray 51 by tray brace bolts 55, which are received into sockets 70, 70' attached to the tray 51or tray frame. The tray 51 is rotatable in relation to the upper tray support adjusting collars 54, 54', so that the tray can be folded parallel to the front main frame members 11, 11' when the overall apparatus is collapsed.

Lower tray support adjusting collars 53, 53' are fastened to the lower ends a pair of tray braces 72, 72' by the lower bolts 55'. A tray spacer tube 59 or 59' surrounds each lower bolt 55' to ensure proper tray spacing and lateral stability; tray braces 72, 72' are pivotal around the bolts 55', since bolts 55' are disposed thorough an aperture in the lower end of each brace. The tray 51 is rotatable in relation to the upper tray support adjusting collars 54, 54', so that the tray can be folded parallel to the front main frame members 11, 11' when the overall apparatus is collapsed. The upper ends of the tray braces 72, 72' are secured to the sides of the tray 51 or tray frame by tray brace bolts 73, 73, which are disposed through apertures in the upper ends of the braces. Tightening the brace bolts 73, 73' into the tray 51 prevents the braces 72, 72' from rotating with respect to the tray 51. With the brace bolts controllably loosened, the braces 72, 72' can pivot around bolts 55'. The entire tray assembly thus can be collapsed easily against the front main frame members 11, 11' by loosening the brace bolts 73, 73', disengaging the lower tray support adjusting collars 53, 53', and sliding them down the frame members 11, 11, and pivoting the braces 72, 72' with respect to both the tray and the lower adjusting collars.

The assembled tray assembly 50 is adjustable in vertical position for maximum accessibility and convenience by an individual supported in the chair. The elevation and pitch of the tray 51 can be regulated and fixed by movably adjusting and temporarily fixing the positions of the tray collars 53, 53, and 54, 54 upon the forward main frame members.

Further, the collapsibility and portability of the apparatus is apparent from the foregoing disclosure. As explained herein above, the frame assemblies 10, 10' can be folded so that the front main frame members 11, 11' are nearly parallel to the rear main frame members 12, 12'. Further, the torso pad adjusting bars 24, 24' can be moved into positions generally parallel to the rear main frame members 12, 12' by manipulating the lockable pivot connectors 28, 28'. The pad 25 can be pivoted, using the torso pad collars 33, 33' to shift into a position roughly coplanar with the plane defined by the rear main frame members 12, 12'. And the tray assembly 50 can be collapsed as described above. In the collapsed condition, the apparatus can be easily carried by a single person, transported in an automobile, or placed in compact storage.

Figure 8:
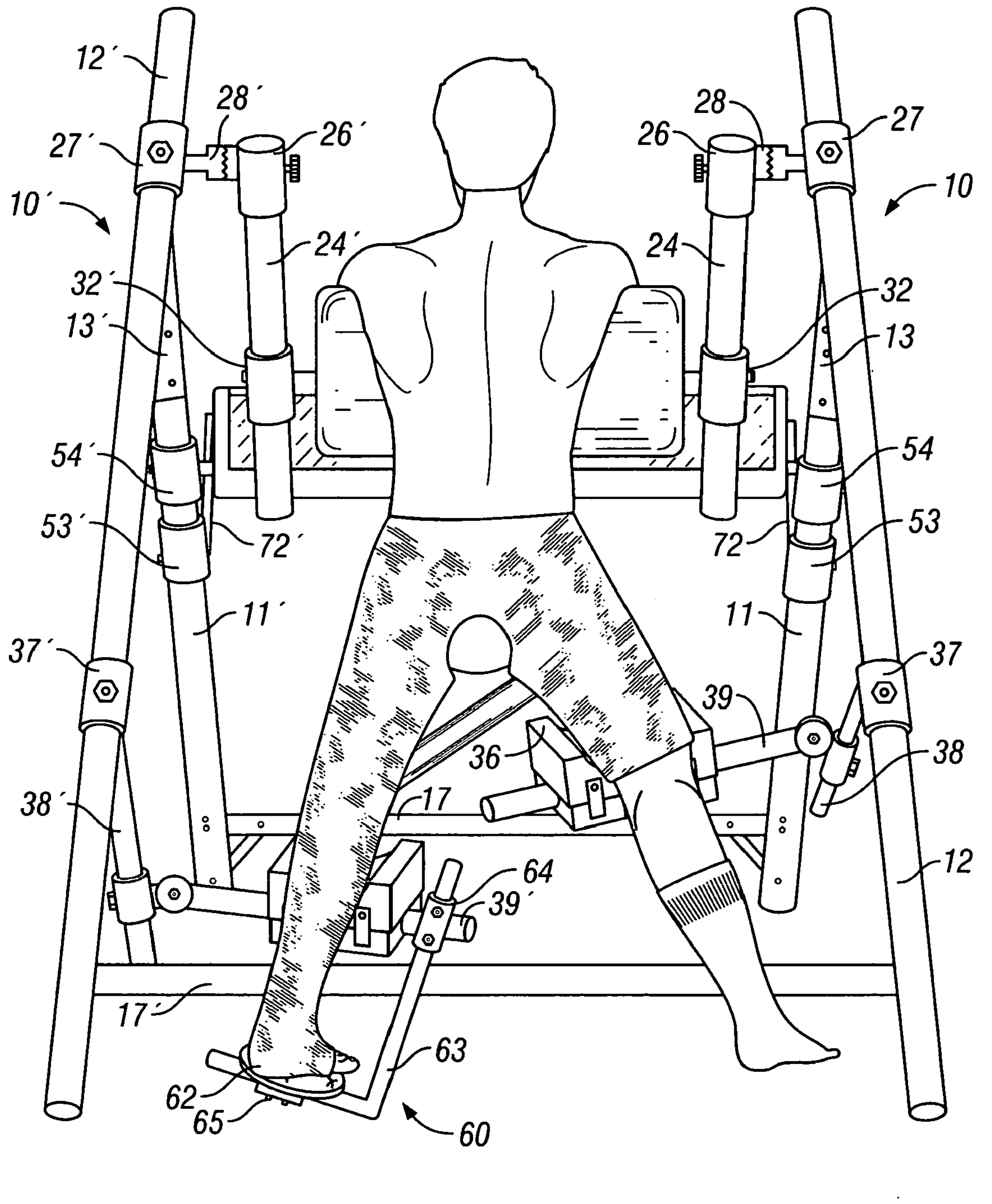
FIG. 8 shows, using phantom lines, a patient using the apparatus of the invention.

Referring to FIGS. 1–3 and especially FIG. 8, it is seen that the patient (usually with the assistance of other persons) assumes a position in which his torso is supported by the torso support pad 25, and his legs are rested in the cradle blocks 36, 36' of the leg assemblies. The torso pad's position can be selected and set according to patient comfort, and the leg assemblies are extremely adaptable in position to receive and accommodate the patient's legs, however they may be positioned and held by the spica cast. The one or both of a foot support pad assembly 60 is positioned and fixed such that the bottom of the patient's foot rests against the pad 62 to maintain the patient semi-erect in the apparatus. Due to the many adjustable collars, the inventive chair can be adjusted precisely to the size and body of the particular patient.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for supporting a person immobilized in a spica cast in a generally upright position, said apparatus comprising:

- a pair of frame assemblies held in spaced apart relation;
- a torso support assembly disposed between and connected to said frame assemblies;
- at least one leg support assembly disposed between and connected to one of said frame assemblies, each said leg support assembly comprising:
  - a leg support adjusting collar movably mounted upon one of said frame assemblies;
  - a leg support adjusting bar connected to said leg support adjusting collar, said leg support adjusting bar being pivotal to, and releasably lockable in, selected angular positions in relation to said leg support adjusting collar; and
- a foot pad support assembly mounted on said leg support assembly;

wherein said foot pad support assembly is selectively adjustable laterally between said frame assemblies.

2. An apparatus according to claim 1 wherein each said frame assembly comprises an A-frame comprised of a rear main frame member and a forward main frame member.

3. An apparatus according to claim 2 wherein said forward frame member is pivotally connected to said rear main frame member and movable between a position extending from said rear main frame member and a collapsed position generally adjacent to said rear main frame member, wherein said A-frame is collapsible.

4. An apparatus according to claim 1 wherein said torso support assembly comprises:

- a pair of torso collar assemblies movably mounted upon respective ones of said frame assemblies;
- a pair of torso pad adjusting bars connected to respective ones of said torso collar assemblies, said torso pad adjusting bars being pivotal to, and releasably lockable in, selected angular positions in relation to said torso collar assemblies;
- a torso pad bar extending between said two torso pad adjusting bars, said torso pad bar being movably connected to said torso pad adjusting bars by pad bar collars, said pad bar collars movably mounted upon said torso pad adjusting bars; and
- a torso pad movably mounted upon said torso pad bar.

5. An apparatus according to claim 4 wherein said pair of torso collar assemblies are movably mounted upon respective ones of said rear main frame members, and are movable to, and releasably lockable at, selected locations along said rear main frame members.

6. An apparatus according to claim 4 wherein said pad bar collars are movable to, and releasably lockable at, selected locations along said torso pad adjusting bars.

7. An apparatus according to claim 4 wherein said torso pad is movable to, and releasably lockable at, selected locations along said torso pad bar.

8. An apparatus according to claim 4 wherein said torso pad is pivotal in relation to said torso pad bar to be movable to, and releasably lockable in, selected angular positions in relation to said torso pad bar.

9. An apparatus according to claim 1 wherein each leg support assembly further comprises:
- a leg cradle adjusting bar extending from said leg support adjusting bar, said leg cradle adjusting bar being movably connected to said leg support adjusting bar by a cradle bar collar, said cradle bar collar movably mounted upon said leg support adjusting bars; and
- at least one cradle block movably mounted upon said leg cradle adjusting bar.

10. An apparatus according to claim 9 wherein said leg support adjusting collar is movably mounted upon one of said rear main frame members, and is movable to, and releasably lockable at, selected locations along said rear main frame member.

11. An apparatus according to claim 9 wherein said cradle bar collar is movable to, and releasably lockable at, selected locations along said leg support adjusting bar.

12. An apparatus according to claim 9 wherein said at least one cradle block is movable to, and releasably lockable at, selected locations along said leg cradle adjusting bar.

13. An apparatus according to claim 9 wherein said at least one cradle block is pivotal in relation to said leg cradle adjusting bar to be movable to, and releasably lockable in, selected angular positions in relation to said leg cradle adjusting bar.

14. An apparatus according to claim 13 wherein said leg support assembly is mounted upon either one of said frame assemblies.

15. An apparatus according to claim 9, wherein said foot support pad assembly is connected to said leg cradle adjusting bar, said foot support pad assembly further comprising:
- an upper pad collar movably disposed upon said leg cradle adjusting bar; an angled stirrup member extending from said upper pad collar; and
- a lower pad collar movably disposed upon said stirrup member; and
- a foot pad attached to said lower pad collar;

wherein said upper pad collar is movable to, and releasably lockable at, selected locations along said leg cradle adjusting bar, and said foot pad is movable to, and releasably lockable at, selected locations along said stirrup member.

16. An apparatus according to claim 13, wherein said at least one cradle block comprises a pair of cradle blocks, independently movable upon said leg cradle adjusting bar.

17. An apparatus according to claim 1, further comprising a tray assembly disposed between and connected to said frame assemblies, said tray assembly connected to said forward main frame members by at least a pair of movable collars, wherein said tray is movable to, and releasably lockable at, selected locations along said forward main frame member.

18. An apparatus for supporting a person immobilized in a spica cast in a generally upright position, said apparatus comprising:
- a pair of frame assemblies held in spaced apart relation;
- a torso support assembly disposed between said frame assemblies, said torso support assembly comprising a movable torso pad selectively positionable laterally in relation to said frame assemblies;
- at least one leg support assembly disposed between said frame assemblies, said leg support assembly comprising;
  - a leg support adjusting collar movably mounted upon one of said frame assemblies:
  - a leg support adjusting bar connected to said leg support adjusting collar, said leg support adjusting bar being pivotal to, and releasably lockable in, selected angular positions in relation to said leg support adjusting collar;
  - a leg cradle adjusting bar extending from said leg support adjusting bar, said leg cradle adjusting bar being movably connected to said leg support adjusting bar by a cradle bar collar, said cradle bar collar movably mounted upon said leg support adjusting bars; and
  - at least one cradle block movably mounted upon said leg cradle adjusting bar.

19. An apparatus according to claim 18 wherein each said frame assembly comprises an A-frame comprised of a forward main frame member pivotally connected to a rear main frame member.

20. An apparatus according to claim 18 wherein said torso support assembly further comprises:
- a pair of torso collar assemblies movably mounted upon respective ones of said frame assemblies;
- a pair of torso pad adjusting bars connected to respective ones of said torso collar assemblies, said torso pad adjusting bars being pivotal to, and releasably lockable in, selected angular positions in relation to said torso collar assemblies; and
- a torso pad bar extending between said two torso pad adjusting bars, said torso pad bar being movably connected to said torso pad adjusting bars by pad bar collars, said pad bar collars movably mounted upon said torso pad adjusting bars;

wherein said torso pad is movably mounted upon said torso pad bar.

21. An apparatus according to claim 20 wherein said pair of torso collar assemblies are movably mounted upon respective ones of said rear main frame members, and are movable to, and releasably lockable at, selected locations along said rear main frame members.

22. An apparatus according to claim 20 wherein said pad bar collars are movable to, and releasably lockable at, selected locations along said torso pad adjusting bars.

23. An apparatus according to claim 20 wherein said torso pad is movable to, and releasably lockable at, selected locations along said torso pad bar.

24. An apparatus according to claim 20 wherein said torso pad is pivotal in relation to said torso pad bar to be movable to, and releasably lockable in, selected angular positions in relation to said torso pad bar.

25. An apparatus according to claim 18 further comprising a foot support pad assembly mounted on said leg support assembly;

wherein said leg support assembly is selectively adjustable to locate said foot support pad assembly anywhere laterally between said frame assemblies.

26. An apparatus according to claim 25 wherein said foot support pad assembly is connected to said leg cradle adjusting bar, said foot support pad assembly comprising:
- an upper pad collar movably disposed upon said leg cradle adjusting bar;

an angled stirrup member extending from said upper pad collar;

a lower pad collar movably disposed upon said stirrup member; and a foot pad attached to said lower pad collar;

wherein said upper pad collar is movable to, and releasably lockable at, selected locations along said leg cradle adjusting bar, and said foot pad is movable to, and releasably lockable at, selected locations along said stirrup member.

27. An apparatus according to claim 18 wherein said leg support adjusting collar is movably mounted upon ones of said rear main frame members, and are movable to, and releasably lockable at, selected locations along said rear main frame members.

28. An apparatus according to claim 18 wherein said cradle bar collar is movable to, and releasably lockable at, selected locations along said leg support adjusting bar.

29. An apparatus according to claim 18 wherein said at least one cradle block is movable to, and releasably lockable at, selected locations along said leg cradle adjusting bar.

30. An apparatus for supporting a person immobilized in a spica cast in a generally upright position above a floor, said apparatus comprising:

a pair of frame assemblies held in spaced apart relation, said assemblies having non-wheeled bottom ends contactable directly with the floor;

a torso support assembly disposed between and connected to said frame assemblies;

a leg support assembly disposed between and connected to one of said frame assemblies, said leg support assembly comprising:

a leg support adjusting collar movably mounted upon one of said frame assemblies;

a leg support adjusting bar connected to said leg support adjusting collar, said leg support adjusting bar being pivotal to, and releasably lockable in, selected angular positions in relation to said leg support adjusting collar; and a leg cradle adjusting bar extending from said leg support adjusting bar, said leg cradle adjusting bar being movably connected to said leg support adjusting bar by a cradle bar collar, said cradle bar collar movably mounted upon said leg support adjusting bars;

wherein the position of said torso support assembly is selectively adjustable in at least two dimensions.

* * * * *